United States Patent [19]  [11] 4,060,639
Jacobus et al.  [45] Nov. 29, 1977

[54] BROAD SPECTRUM ANTIBACTERIAL COMPOSITIONS CONTAINING TRIS-(HYDROXYMETHYL)-AMINOETHANE AND DICYCLOALIPHATIC-ALKYL POLYAMINES

[75] Inventors: David P. Jacobus, Princeton; Eugene L. Dulaney, Summit; Nathaniel Grier, Englewood, all of N.J.

[73] Assignee: Merck & Co., Inc., Rahway, N.J.

[21] Appl. No.: 686,428

[22] Filed: May 14, 1976

[51] Int. Cl.² .................. A01N 9/02; A01N 9/20; A01N 9/22
[52] U.S. Cl. ................................. 424/325; 424/250
[58] Field of Search ................. 71/67; 424/250, 325

[56] References Cited

U.S. PATENT DOCUMENTS

| | | | |
|---|---|---|---|
| 2,781,398 | 2/1957 | Morren | 260/570.5 |
| 3,064,052 | 11/1962 | Goldberg et al. | 260/563 |
| 3,466,162 | 9/1969 | Gloor et al. | 71/67 |
| 3,862,330 | 1/1975 | Johnson et al. | 424/330 |
| 3,874,869 | 4/1975 | Koppensteiner et al. | 71/67 |

FOREIGN PATENT DOCUMENTS 844,827   8/1960   United Kingdom.

OTHER PUBLICATIONS

Voss, Journal General Microbiology 48 pp. 391–400, (1967).
American Cyanamid; C.A. 57:16,398g (1962).
Short et al., C.A. 59:8609f (1963).
Pratesi et al; C.A. 63:11,395q, (1965).
Maggioni & C. Societa per Azionic; C.A. 58:5698d, (1963).

*Primary Examiner*—Allen J. Robinson
*Attorney, Agent, or Firm*—Edmunde D. Riedl; Julian S. Levitt

[57] ABSTRACT

A composition comprising tris-(hydroxymethyl) aminomethane and dicyclohexyl-, dicyclohexenyl- and cyclohexylcyclohexenyl-alkyl polyamines, their acid addition salts, and mixtures thereof are useful as antibacterial agents. The composition is particularly useful because of the synergistic improvement obtained against strains of the genus Pseudomonas, as well as other genera.

24 Claims, No Drawings

BROAD SPECTRUM ANTIBACTERIAL COMPOSITIONS CONTAINING TRIS-(HYDROXYMETHYL)-AMINOETHANE AND DICYCLOALIPHATIC-ALKYL POLYAMINES

DISCLOSURE OF THE INVENTION

This invention relates to antibacterial compositions. More particularly, this invention relates to compositions comprising an admixture of tris-(hydroxymethyl)aminomethane and either individually or in combination a polyamine having the structural formula:

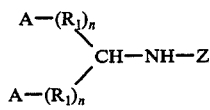
(I)

where A is independently a cyclohexyl or $C_1$ to $C_6$ alkyl substituted cyclohexyl, or an unsubstituted or $C_1$ to $C_6$ alkyl substituted cyclohexenyl of the formula:

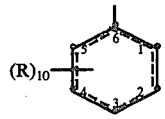

where each R is either hydrogen or $C_1$ to $C_6$ alkyl and the dashed line indicates either saturation or a single olefinic bond in the ring and provided that if A is cyclohexenyl, no more than 9 of R are $C_1$ to $C_6$ alkyl.

Most suitably, less than five of R are $C_1$ to $C_6$ alkyl and preferably the total of carbon atoms in all of the R groups does not exceed eight. Most preferably, only three of the R groups are $C_1$ to $C_4$ alkyl, and as such are desirably methyl or ethyl.

Each $n$ is alike or different and is the integer 0 or 1;
Each $R_1$ is alike or different and is $C_1$ to $C_4$ alkylene;
Z is

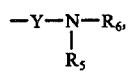

where
$R_5$ is hydrogen, aminoethyl, aminopropyl, $C_1$ to $C_4$ hydroxyalkyl, or $C_2$ to $C_4$ dihydroxyalkyl; and
$R_6$ is hydrogen, $C_1$ to $C_4$ hydroxyalkyl or $C_2$ to $C_4$ dihydroxyalkyl; and
Where Y is

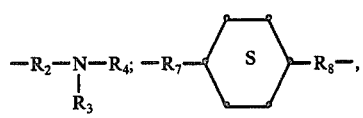

or $R_2$.
When Y is

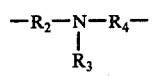

$R_2$ is 2-hydroxy-1,3-trimethylene, or $R_1$ as previously defined;

$R_3$ is hydrogen, $C_1$ to $C_4$ alkyl, $C_2$ to $C_4$ aminoalkyl or $C_1$ to $C_4$ hydroxyalkyl, $C_2$ to $C_4$ dihydroxyalkyl, e.g., 2,3-dihydroxypropyl and 3,4-dihydroxybutyl;

$R_4$ is 2-hydroxy-1,3-trimethylene, or $R_1$ as previously defined;

or when $R_3$ and $R_6$ taken together are ethylene, $R_4$ is also ethylene, and $R_5$ is aminoethyl, aminopropyl, or aminohydroxypropyl;

When Y is

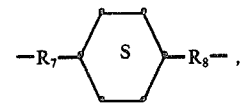

$R_7$ is $R_2$, methylene, or a chemical bond between the cyclohexylene moiety and a first nitrogen; $R_8$ is $R_4$ methylene or a chemical bond between the cyclohexylene moiety and a second nitrogen;

When Y is $-R_2-$, $R_2$, $R_5$ and $R_6$ are as previously defined. Most suitably $R_3$, $R_5$ and $R_6$ are not simultaneously dihydroxyalkyl, and when $R_3$, $R_5$ and $R_6$ are simultaneously dihydroxyalkyl, it is preferable that they are $C_3$ or $C_4$ dihydroxyalkyl, and optionally their acid addition salts particularly the hydrochloride. Preferred polyamines I are those where the sum of the carbon atoms in both of $R_1$ are from 2 to 8.

The antibacterial composition comprises at least 0.5 part by weight of the tris-(hydroxymethyl)aminomethane for each part by weight of the polyamine expressed as the base compound, and more prferably from 1 to 500 parts of the tris-(hydroxymethyl)aminomethane. Generally, the combination of trisamine and polyamine is combined in a suitable solvent or dispersant as a carrier. Such solvents or dispersants, for example, are usually polar and those such as water, lower alkylene glycol, or lower alkanols including amyl alcohol are especially suitable as well as in mixtures of such solvents. Such inclusion of the antibacterial combination in a suitable solvent is not required to produce the synergistic action, but is merely a convenience when using the combination as an antibacterial agent. In fact, an excess of tris-(hydroxymethyl)aminomethane can conveniently be employed as an admixture with salts of the polyamines in powders, suspensions, or solutions.

In formulations including the synergistic composition of this invention, it is suitable to include other antibacterial agents, suspending agents, wetting agents, antiscaling agents, corrosion inhibitors, and pH control agents such as the usual buffers commonly employed to achieve a desired pH. Therefore, alkali silicates, alkali phosphates, alkali gluconates, polyphosphates, and pyrophosphates, organic amines, polyamines, and polyamides; anionic, cationic and non-ionic wetting agents; alkali carbonates, bicarbonates, sulfates, sesquicarbonates; and the like can suitably be included in the final formulation.

In use, the antibacterial composition can be applied as a rinse, a drench, or if employed as a cleanser for skin can be used as a soap, a cream, or a foaming composition. If desired, the material can also be packaged in aerosol form and sprayed on surfaces where antibacterial control is desired. In addition, the material can be used to impregnate fabrics, woven or nonwoven to render them bacteriostatic.

One especially desirable application is its use in floor and wall cleaning formulations wherein the antibacterial composition, preferably including also pH control agents, wetting agents, and those other agents that are commonly found in floor cleaning formulations is further diluted with water and applied by mopping, swabbing or other conventional means.

Acid addition salts of one or more amino functions of the triazaalkane or tetraazaalkane moiety of the polyamine can be employed. Suitable anions for the salt include anions derived from inorganic acids as well as those of organic acids such, for example, as halide, i.e., chloride, bromide or iodide or sulfate, nitrate, bisulfate, phosphate, acetate, propionate, maleate, succinate, laurate, palmitate, oleate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like. Generally, any anion derived from an acid is suitable and satisfactory when the polyamine salt anion, for example, the chloride is replaced with other anions, by well known anion exchange techniques. Most suitably, the chloride salt is passed through an anion exchange resin.

In a preferred embodiment of this invention, an antimicrobial composition of polyamine, e.g., 1-[1,5-di-(3,3-dimethylnorborn-2-yl)-3-pentyl]-1,5,9-triazanonane trihydrochloride admixed with tris(hydroxymethyl)aminomethane provides upon solution in aqueous media a concentration of 1-100 ppm of polyamine salt and 1000-5000 ppm of tris(hydroxymethyl)aminomethane. Whereas the polyamine salt by itself is capable of inhibiting gram negative and gram positive bacteria at such dilutions, various strains of Proteus and Serratia appear unaffected. In the presence of the tris(hydroxymethyl)aminomethane they are controlled by the polyamine even at its lower concentration range. Moreover, only about one-half to one-tenth the inhibitory concentrations of polyamine is needed in combination to suppress *Pseudomonas aeruginosa* and *Staphylococcus aureus* as compared to the polyamine alone.

The following examples show methods for preparing the polyamines of this invention as typical of those that can be used in applications employing the synergistic composition of this invention.

The compounds of this invention are preferably prepared according to the following sequence of reactions:

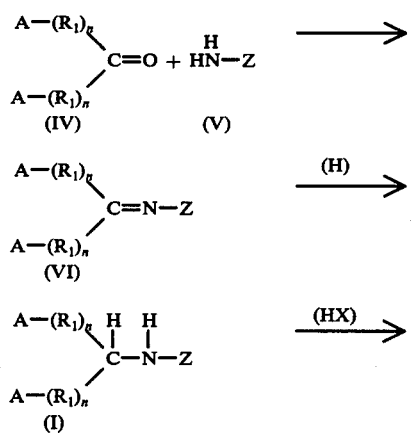

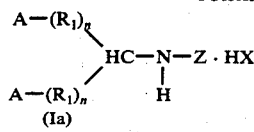
(Ia)

where A, Z and $n$ have their previously defined meanings, HX is a mono or polybasic organic or inorganic acid, where sufficient HX is provided to protonate at least one amino group of compound I.

The preparation of polyamine I comprises the straightforward Schiff base reaction of the appropriate ketone IV and the appropriate amine V.

If amine V has two primary amino groups, it can either be symmetrical or unsymmetrical. An amine V, which is a symmetrical amine, e.g., where $R_2$ and $R_4$ are alike when $R_5$ and $R_6$ are hydrogen; or where $R_2$ and $R_4$ are ethylene, $R_5$ is aminoethyl, and $R_6$ is hydrogen; or where $R_2$ is trimethylene when $R_5$ is 3-aminopropyl and $R_6$ is hydrogen; forms a single Schiff base VI. This is because regardless of which terminal primary amino group of amine V reacts with ketone IV, the same product results. However, where amine V is unsymmetrical two products can result. One is Schiff base VI. The other products have the formula VI(a) when $R_5$ and $R_6$ are hydrogen;

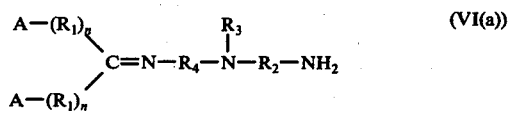

or VI(b) when $R_5$ is aminoethyl or aminopropyl;

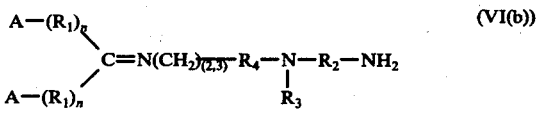

where A, $R_{1-6}$ and $n$ are as previously defined. Note that both products VI(a) and VI(b) come within the scope of the definition given for Schiff base VI. Where Schiff bases of formulas VI and VI(a) or VI(b) are produced they can be separated, if desired, by the usual and well known separation techniques, i.e., distillation and the like.

As an alternative to obtaining a mixture of Schiff bases VI and VI(a) or VI(b), the reaction can be conducted stepwise. For example, 1,2-diaminoethane may be converted to a Schiff base with 1,5-di-(4-isopropylcyclohexyl)-3-pentanone, catalytically reduced, then the ring nitrogen selectively cyanoethylated with acrylonitrile, followed by catalytic hydrogenation to furnish [1,5-di-(4-isopropylcyclohexyl)-3-pentyl]-1,4,8-triazaoctane.

To prepare Schiff base VI, ketone IV and amine V are dissolved in a suitable inert solvent, for example, toluene, and heated to reflux, until reaction is substantially complete. Usually 5 to 20 hours is sufficient for water removal by azeotropic distillation. The solvent is then removed under reduced pressure and the residue comprising the Schiff base VI is dissolved in an inert solvent preferably an alkanol, such as ethanol or isopropanol.

After dissolution, the Schiff base VI is catalytically or chemically reduced.

If reduction is catalytic, any unsaturated carbon to carbon bond in A will also be reduced or hydrogenated, as well as the carbon to nitrogen bond of the Schiff base VI. In such catalytic reductions, hydrogen saturates an alkanol solution of Schiff base VI using agitation in the presence of the usual hydrogenation catalysts, such as transition metals and their reducible oxides. Especially effective catalysts are the noble metals and their oxides. A particularly preferred catalyst is platinum oxide. Generally, the hydrogenation reaction is carried out in a manner well known in the art. Small particles, e.g., 100–300 mesh of catalyst are admixed with the Schiff base and excess amine in alcohol and placed in a closed system pressurized with from 3–5 atmospheres of hydrogen gas preferably at ambient temperature, and generally at such pressures and a temperature of from 15° C. to 45° C. At higher temperatures the pressure preferably need not exceed 15 atmospheres. After reaction is complete, the pressure is released and the catalyst separated from the reaction mixture by filtration. The filtrate containing the cyclohexyl polyamine I, is then further purified by usual techniques. Preferably, whatever solvent may be present is removed under reduced pressure, the residue then dissolved in a water-immiscible solvent, washed with water, followed by a further washing with a saturated aqueous inorganic salt solution. After drying, the solvent is removed by evaporation under reduced pressure giving the cyclohexylpolyamine I usually as an oil. The cyclohexylpolyamine can then be redissolved in loweralkanols, mixtures of loweralkanols and water, diethylether, dioxane and then neutralized with an acid, e.g., hydrogen chloride, or neutralized directly with aqueous acids.

Acid addition salts are then isolated, if desired, by precipitation, evaporation or other usually employed techniques.

Suitable anions X for the salt I($a$) include anions derived from inorganic acids as well as those of organic acids such for example as halide, i.e., chloride, bromide or iodide or sulfate, nitrate, bisulfate, phosphate, acetate, propionate, maleate, succinate, laurate, palmitate, oleate, stearate, ascorbate, gluconate, citrate, carbonate, bicarbonate, benzoate, salicylate, pamoate, phthalate, furoate, picolinate, dodecylbenzenesulfonate, laurylethersulfonate, nicotinate and the like. Generally, any anion derived from an acid is suitable and satisfactory when the polyamine salt anion X−, e.g., chloride is replaced with other anions, by well known anion exchange techniques.

When preparing cyclohexenylpolyamines, that is the product I where olefinic unsaturation in ring A is retained, a selective chemical rather than a catalytic reduction is employed to reduce Schiff base VI to product I.

In this chemically reductive procedure, the ketone IV is reacted with the appropriate amine as before, but the Schiff base VI dissolved in an inert alkanol or ether-type solvent is reacted with a chemical reductant such as sodium borohydride or lithium aluminum hydride, respectively.

Although as little as an equivalent of the chemical reductant can be used successfully, more satisfactory results are obtained if at least two molar excess of and preferably at least a 2.5 molar excess of the chemical reductant is employed. After any initial reaction has subsided, the reaction mixture of Schiff base VI and reductant may be heated to reflux for an hour or two, then cooled to room temperature, and afterwards concentrated under vacuum. The residue obtained is then further purified as by treatment with mineral acid or inorganic base as was described for polyamines I and the salt may thereafter be formed as previously described.

The cyclohexyl and cyclohexenyl ketones IV are readily prepared and two alternative methods, are set forth below.

A. The Condensation of Acids

This method involves the following reaction scheme:

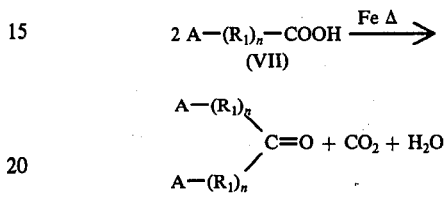

Acylative decarboxylation of acids VII is employed by heating the acid at elevated temperatures either with transition metals, preferably iron, transition metal oxides, alkaline earth oxides, with polyphosphoric acid or with boron trifluoride. Most suitably, acylative reaction is achieved by passage of acid vapors over catalysts such as heated thoria aerogel.

Condensation-decarboxylation of an acid is the preferred method for preparing ketone IV when each A-$(R_1)_n$ group is alike, a mixture of products being obtained when several different acids are combined in a reaction. The preferred reaction comprises admixing carboxylic acid VII with reduced iron powder and stirring in an inert atmosphere at 195° C. to 200° C. for 1–6 hours to form an iron salt.

Preferably, the carboxylic acid VII and iron are agitated under an inert atmosphere of nitrogen for at least 2 hours at 195° C. to 200° C.

After 2 hours, the temperature is increased suitably to 290° C. to 310° C. and agitation continued for at least another three hour period, four hours usually being sufficient. The reaction mixture is allowed to cool, and then is extracted with a suitable inert solvent such as diethylether and filtered. The solvent extracts are concentrated under reduced pressure. The residual liquid is distilled under vacuum to isolate the ketone IV.

The carboxylic acids VII employed above are prepared by various means well known in the art. One particularly useful technique is the addition of a cyclohexene to an aliphatic acid anhydride.

In this procedure, a mixture of the cyclohexene and a catalytic quantity, e.g., 0.2–0.3 mole for each mole of cyclohexene of a free radical-forming catalyst, such as di-tert-butyl peroxide, is added dropwise over 3–5 hours to a 5–15 molar excess of refluxing aliphatic acid anhydride. After complete addition, the reaction is heated at reflux for 5–10 hours, concentrated under reduced pressure and the liquid residue is mixed with aqueous sodium hydroxide and stirred with heating on a steam bath for about 2–5 hours. The cooled alkaline solution is then extracted with ether, the ether layer is discarded and the aqueous solution acidified, and then extracted well with ether. The combined ether extracts are washed with water, dried over anhydrous sodium sulfate, and concentrate under reduced pressure. The residual liquid or solid is distilled under vacuum to give the corresponding carboxylic acid, VII.

Other carboxylic acids are readily obtained, for example, by the Diels-Alder reaction of a diene and alkyl substituted diene with various unsaturated aliphatic compounds or carboxylic acids, as are later referred to in greater detail.

B. Condensation of a Grignard and a Nitrile

Dicyclohexyl, dicyclohexenyl, or cyclohexyl-cyclohexenyl alkanones can be obtained according to the following reaction scheme:

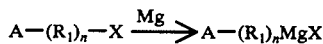

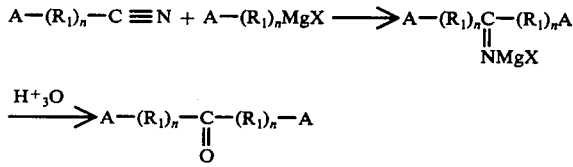

where A or $(R_1)_n$ of each reactant may be the same or different and are as previously defined.

This general procedure utilizes the reaction of a Grignard reagent prepared from a chloro- or bromo-substituted cyclohexane or cyclohexene derivative with a cyanosubstituted cyclohexane or cyclohexene derivative. The resultant disubstituted iminoalkane salt complex is hydrolyzed with aqueous mineral acid to the corresponding ketone.

The Grignard reagent is obtained by reaction of the halide with magnesium metal, usually in the form of turnings or powder and may be catalyzed by very small concentrations of iodine or methyl iodide. Solvents which are useful include diethyl ether, dibutyl ether, tetrahydrofuran, dioxane and benzene. Usually, gentle warming suffices to initiate the reaction and the halide is gradually added to the metal-solvent mixture. After complete addition the diappearance of practically all magnesium metal signifies the end of the reaction. A small excess of halide is used and moisture must be excluded; a nitrogen atmosphere is beneficial. The Grignard reagent is then added to the nitrile which is previously dissolved in two or three times its volume of solvent over a period of 15 minutes to 1 hour at ambient temperature. The reaction mixture may then be heated to reflux to insure complete reaction. Generally, a small excess of Grignard reagent as compared to nitrile is employed. From 1 to 10 hours at reflux is sufficient for complete conversion. The resultant imine salt is preferably decomposed to the ketone with aqueous mineral acids such as hydrochloric, sulfuric and phosphoric. The ketones are water-insoluble and may be extracted with water-immiscible solvents. Purification is preferably accomplished by fractional distillation under reduced pressure. It is feasible to use the crude ketone reaction mixture for the alkylation of polyamines as the reaction by-products are usually alcohols or hydrocarbons and do not react with amines. The reactant halides, if present in the crude product, should be removed prior to the ketone-amine alkylation process.

The concentration of Grignard reagent and nitrile may be varied over wide limits for securing good yields in the process.

The halide and cyano, as well as carboxylic derivatives of cyclohexanes and cyclohexenes are commonly available; where the requisite carboxylic, cyano or halo derivatives are used herein are not readily available they can be obtained through employing known techniques, for example, by means of the Diels-Alder synthesis:

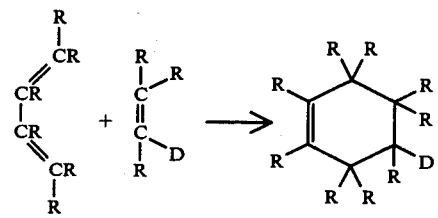

where D is R, $-(R_1)_n-COOH$, $-(R_1)_n-Br$, or $-(R_1)_n-CN$ and where $R_1$, R, and X have their previous meanings. Where D is R and each R is alkyl, the resulting cyclohexene can be reacted with an aliphatic acid anhydride as previously described. Where D is $(R_1)_n-COOH$, $(R_1)_n-CN$ or $(R_1)_n-BR$, the condensation can proceed as outlined in preparative examples A and B above. Of course, $A(R_1)_n-COOH$ can be treated by standard techniques with a phosphorous chloride, e.g., phosphorous pentachloride, to form $A(R_1)_n-COCl$.

Where R is independently either hydrogen or $C_1$ to $C_6$ alkyl, the Darzens synthesis [Compt. Rend., 150, 707 (1910)] can be used.

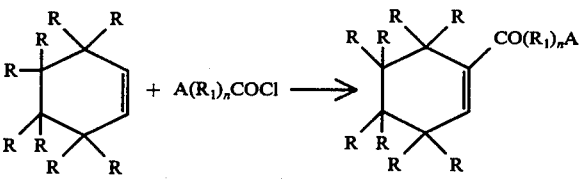

where $R_1$, n, R and A are as previously defined. Likewise, the Blaise-Marie synthetic route can be employed [Bull. Soc. Chim. [4] 7, 215 (1910) and Compt. Rend. 145, 73 (1907)]:

where A, n and $R_1$ have their previously defined meanings.

Once the ketone IV is obtained it can then be reacted with a suitable polyamine V. Polyamines V which are exceptionally suitable for reaction with ketone IV include diethylenetriamine, triethylenetetramine, 3,3'-iminobis(propylamine), 3,3'-methyliminobis-(propylamine), dipropylenetriamine, N,N'-bis-(3-aminopropyl)-1,3-trimethylenediamine, N,N'-bis-(2-aminoethyl)-1,3-trimethylenediamine, N,N'-bis-(3-aminopropyl)piperazine, N-(3-amino-2-hydroxypropyl)-1,3-trimethylenediamine, N-(2-aminoethyl)-1,3-trimethylene-diamine, spermidine, spermine, 1,4-bis-(2-aminoethyl)piperazine, tris-(2-aminoethyl)amine, 1-(2-aminoethyl)-4-(3-aminopropyl)piperazine, 1-(3-amino-2-hydroxypropyl)-4-(2-aminoethyl)piperazine, N-(3-amino-2-hydroxypropyl)-1,3-trimethylenediamine, N,N'-bis-(3-aminopropyl)-1,4-cyclohexylene-bis-(methylamine), 1-(2,3-dihydroxypropyl)-1,5,9-triazanonane, 1-(2-hydroxyethyl)-1,4,7,10-tetraazadecane, 4-(3,4-dihydroxybutyl)-1,4,8-triazaoctane, 1-(2-hydroxypropyl)-5-hydroxymethyl-1,5,9-triazanonane, 1,4-di-(3-aminopropyl)piperidine, tris-(3-aminopropyl)amine, ethylenediamine, trimethylenediamine, and 1,3-diamino-2-hydroxypropane.

PREPARATION A

Free Radical Addition of Acetic Anhydride to β-Pinene

To 1,000 g. (10 moles) of refluxing acetic anhydride is added dropwise a mixture of 136 g. β-pinene (1.0 mole) and 30 g. t-butyl peroxide (0.2 mole) over a period of 2.5 hours. The reaction mixture is then heated at reflux for an additional 5 hours. The acetic anhydride is then removed under vacuum and the residue hydrolyzed by treatment with 40 g. NaOH in 250 ml. water and 150 ml. ethanol. The mixture is heated at reflux for 2 hours, then acidified with hydrochloric acid, extracted with ether and dried over sodium sulfate. The dried extracts are evaporated to leave a residue which is distilled under vacuum giving 43.1 g. (22%) of 3-(4-isopropylcyclohexenyl)propionic acid having a b.p. 135°–137° C. (0.3 mm.).

PREPARATION B

3-(4-Isopropylcyclohexyl)propionic Acid

The unsaturated acid from the previous preparation is dissolved in ethanol and hydrogenated with PtO$_2$ at room temperature and 40 psi hydrogen pressure. The platinum catalyst is filtered off and the ethanol removed under reduced pressure. The saturated product 3-(4-isopropylcyclohexyl)propionic acid is obtained as a colorless liquid 42.3 g. (97%).

PREPARATION C

Preparation of 1,5-Di-(4-Isopropylcyclohexyl)-3-pentanone 3-(4-Isopropylcyclohexyl)propionic acid (39.7 g., 0.20 mole) and iron (hydrogen reduced, 6.15 g., 0.11 mole) is heated for 1.5 hours at 195° C. under a nitrogen atmosphere. After that time, the temperature is increased to 290° C. and maintained at that temperature for 3 hours. The cooled reaction mass is extracted well with ether, filtered through Celite, and the ethereal extracts concentrated under vacuum. The residue is stripped under vacuum to leave the product, 17.3 g. (51%).

Similarly in an analogous manner there are obtained the following ketones.

1,9-Dicyclohexyl-5-nonanone;
1,5-Dicyclohexyl-3-pentanone;
1,3-Dicyclohexylacetone;
1,7-Dicyclohexyl-4-heptanone;
1,3-Di-(3-methylcyclohexyl)acetone;
1,7-Di-(4-ethylcyclohexyl)-4-heptanone;
1,5-Di-(2-isopropylcyclohexyl)-3-pentanone;
1,9-Di-(2-ethylcyclohexyl)-5-nonanone;
1,5-Di-(4-t-butylcyclohexyl)-3-pentanone;
1,5-Di-(2,4,6-trimethylcyclohexyl)-3-pentanone;
1,5-Di-(3,5-diethylcyclohexyl)-3-pentanone;
1,7-Di-(2,6-dimethyl-4-t-butylcyclohexyl)-4-heptanone;
1,7-Di-(2,3,4,5,6-pentamethylcyclohexyl)-4-heptanone;

when unsaturated acids are subjected to the above procedure the following representative ketones are obtained:

1,7-Dicyclohex-3-enyl-4-heptanone;
2,8-Di-(4-methylcyclohex-3-enyl)-5-nonanone and
1,5-Di-[4-isopropylcyclohex-1-enyl]-3-pentanone.

PREPARATION D

Preparation of 4-Cyclohexyl-1-(4-isopropylcyclohexyl)-butanone-2

A Grignard reagent was prepared from 2-cyclohexylethyl bromide 21 gm. (0.11 mole) and magnesium, 2.4 g. (0.1 gram atom). The magnesium is covered with 25 ml. of anhydrous ether, a crystal of iodine added and in a nitrogen atmosphere, the halide dissolved in 50 ml. of anhydrous ether is added, once initial reaction is obtained, at reflux temperature over a period of 1-2 hours. After complete addition, refluxing is continued for ½ hour.

In a nitrogen atmosphere, the Grignard solution is clarified by passage through a glass wool filter plug and added slowly to an agitated solution of 4-isopropylcyclohexylacetonitrile, 14.9 gm. (0.09 mole) in 200 ml. of anhydrous diethyl ether. A gentle reflux is maintained during the addition which requires ½ to 1 hour. After complete addition and an additional 15 minutes at reflux, the reaction mixture is cooled and poured onto a mixture of 50 ml. of concentrated hydrochloric acid and 200 gms. of ice using good mixing. Upon warming the ether is removed by distillation and the residue heated at 70°–100° C. for 1 hour. The product is extracted with two portions, 250 ml. each of ether, the ether solution dried over anhydrous magnesium sulfate and the solvent removed. Any of the reactants, i.e., halide and nitrile, are separated from the ketone by fractional distillation under reduced pressure along with by-products.

In a similar procedure, the following ketones are prepared:

1-(2-Methylcyclohexyl)-4-cyclohexylpentan-2-one;
1-(4-t-Butylcyclohexyl)-5-(4-isopropylcyclohexyl)pentan-3-one;
2-(3-Methylcyclohexenyl)-8-(2-isopropylcyclohexyl)octan-4-one;
1-(2,6-Dimethyl-4-t-butylcyclohexyl)-5-(3,5-diethylcyclohexyl)pentan-3-one.

PREPARATION E

Preparation of N-(3-Aminopropyl)-1,4-cyclohexanebis(methylamine)

Acrylonitrile (26.5 g., 0.5 mole) is added dropwise over a 45 minute period to 1,4-cyclohexanebis(methylamine) (2.84 g., 2.0 mole) with stirring and ice bath cooling. After complete addition, the reaction mixture is stirred an additional 1 hour at 5° C., gradually warmed to 45° C. and kept 2 hours at that temperature followed by 1 hour at 90° C. The reaction mixture is stripped of any unreacted acrylonitrile and excess non-cyanoethylated bis(methylamine) starting material which was removed at an internal temperature of 110° C. and 1 mm. The residue is then dissolved in 1.5 l. of ethyl alcohol (ammonia gas saturated) mixed with 50 ml. of sponge nickel catalyst and hydrogenated at 150 psi. After removal of catalyst by filtration, the solvent and ammonia is stripped off and the triamine product purified by fractionation under reduced pressure.

A higher homolog, N-(3-aminopropyl)-1,4-cyclohexanebis-(2-ethylamine) is synthesized using the above procedure with 1,4-bis-(2-aminoethyl)cyclohexane prepared according to P. P. Garcia and J. H. Wood, *J. Org.*

*Chem.*, 26, 4167 (1961). Excess staring amine in this example may be separated from product at a boiling point of 122°–126° C./1 mm.

PREPARATION F

Preparation of N-(3-Aminopropyl)-N'-(2-hydroxyethyl)-1,4-cyclohexanebis(methylamine)

Acrylonitrile (10.6 g., 0.2 mole) is added dropwise over a 15 minute period to N-(2-hydroxyethyl-1,4-cyclohexanebis(methylamine) (37.2 g., 0.4 mole) with stirring and ice bath cooling. After complete addition, the reaction mixture is stirred an additional 2 hours at 5° C., allowed to gradually warm over a 1 hour period, heated 2 hours at 45° C. and finally 1 hour at 90° C. It is then fractionated under reduced pressure up to an internal temperature of 170° C. The residue is dissolved in 200 ml. ethyl alcohol, cooled in an ice bath and saturated with ammonia gas at 0° C. Approximately 5 ml. of sponge nickel catalyst (W. R. Grace Co., Davison Chem. Division) is added and the mixture shaken under hydrogen at 150 psi until no further hydrogen uptake. The catalyst is removed by suction, filtration under nitrogen, the solvent stripped away and the residue fractionally distilled under reduced pressure. The triamine product is readily distinguished from cyanoethylated diamine by its lower $R_f$ on silica gel using a solution of 1 volume concentrated aqueous ammonium hydroxide in 4 volume methyl alcohol. The synthesis is an adaptation of the method of M. Israel et al, *J. Med. Chem.*, 7, 710 (1964) for the preparation of polymethylenepolyamines.

PREPARATION G

Preparation of N-(2-Hydroxyethyl)-1,4-cyclohexanebis(methylamine)

A solution of 14.2 gm. (0.1 mole) of 1,4-cyclohexanebis(methylamine) in 150 ml. anhydrous methyl alcohol and under an atmosphere of nitrogen is warmed to 45° C.–50° C. In a 20 minute period, there is introduced with good agitation and beneath the liquid surface a total of 1.1 gm. (0.025 mole) of ethylene oxide in gaseous form. The reaction temperature is maintained at 45° C.–50° C. for an additional one-half hour after stopping the addition of ethylene oxide. The methyl alcohol is removed by distillation at atmospheric pressure; excess 1,4-cyclohexanebis(methylamine) is readily separated from the product by fractionation under reduced pressure. Only monoethoxylated compound remained and could be used as such or further purified by distillation at reduced pressure.

PREPARATION H

Preparation of N-(3-Amino-2-hydroxypropyl)-1,4-cyclohexanebis(methylamine)

1,4-Cyclohexanebis(methylamine) (14.2 g., 0.1 mole) is dissolved in 50 ml. of anhydrous methyl alcohol and the solution cooled to +5° C. in an ice bath. Epichlorohydrin (9.3 g., 0.1 mole) is added in a 2-minute period and the temperature maintained at +5° C. for 2 hours; reaction is allowed to continue at 10° C–15° C. until thin layer chromatography of an aliquot (silica gel plate with development using a solution of 1 volume concentrated aqueous ammonium hydroxide in 4 volumes of methyl alcohol) indicated nearly complete conversion of the starting diamine to the propylene chlorohydrin. The solution is then added to 100 ml. of dry methyl alcohol previously saturated at 0° C. with dry ammonia gas by continuous dropwise flow at +5° C. with good agitation and external cooling. After stirring 2 hours at +5° C., it is allowed to warm to 20° C. and mixed overnight. The reaction is completed by heating at 45° C.–55° C. for 6 hours. The solvent and ammonia was removed by stripping and the product purified using fractional distillation under reduced pressure.

N-(2,3-Dihydroxypropyl)-1,4-cyclohexanebis(methylamine) is produced by alkaline hydrolysis of the above propylenechlorohydrin derivative.

The propylene chlorohydrin derivative is dissolved in a 1M sodium hydroxide solution containing 50% methyl alcohol and 50% water by weight in a ratio of 5 grams of chlorohydrin to 25 ml. of sodium hydroxide solution. After stirring 24 hours at 20° C. the methyl alcohol is removed by distillation and the oil which separates is extracted with 100 ml. of diethyl ether. The extract is washed with approximately 10 ml. of cold water, the ether layer dried over anhydrous sodium sulphate and then filtered. Removal of the ether by distillation leaves the product in good purity as an oil.

PREPARATION I

Preparation of N,N'-bis-(3-Aminopropyl)-1,4-bis-(2-aminoethyl)cyclohexane

Acrylonitrile (10.6 g., 0.2 mole) is added dropwise over a 15 minute period to 1,4-bis-(2-aminoethyl)cyclohexane (17.0 g., 0.1 mole) cooled in an ice bath and with good stirring. The resultant solution is maintained at 5° C.–10° C. with agitation for 1 hour, allowed to warm to 25° C. over a 2 hour period and finally heated at 90° C.–95° C. for 4 hours. The reaction mixture is then freed of any unreacted material and monocyanoethylated product by gradually heating to an internal temperature of 130° C. at a pressure of 0.5–1 mm. The residue is dissolved in 200 ml. ethyl alcohol which had been previously saturated with dry ammonia gas at 0° C., mixed with approximately 5 ml. of a sponge nickel catalyst suspension and reduced with shaking under 200 psi hydrogen. The catalyst is removed by suction filtration, the filtrate stripped of solvent and the residue purified by fractional distillation under reduced pressure.

PREPARATION J

Preparation of N-(2-Aminoethyl)-1,4-bis-(2-aminoethyl)cyclohexane 1,4-Bis-(2-aminoethyl)cyclohexane (68 gm., 0.4 mole) and ethyleneimine (4.3 gm., 0.1 mole) with 0.4 g. ammonium chloride are mixed in a glasslined pressure reactor and filled with nitrogen to 100 psi. The mixture is shaken and heated at 85° C.–95° C. for 48 hours. After cooling, it is distilled rapidly free of the salt and then fractionated under high vacuum. The starting diamine is readily distinguished from the triamine product by thin layer chromatography on silica gel using a mixture of 1 volume concentrated aqueous ammonium hydroxide with 4 volume methyl alcohol, the diamine having a much higher $R_f$.

PREPARATION K

N,N-Bis-(3-hydroxypropyl)-1,4-cyclohexanebis(methylamine)

Preparation of 1-Cyano-4-[di-(3-hydroxypropyl)aminomethyl]-cyclohexane and catalytic reduction a. 1-Bromomethyl-4-cyanocyclohexane (20.2 g., 0.1 mole) and di-(3-hydroxypropyl)amine (53.2 g., 0.4 mole) in 400 ml. of anhydrous isopropyl alcohol are heated in an autoclave at 105° C.–115° C. for 8 hours with continuous agitation. The reaction mixture is stripped of solvent under reduced pressure and the residue diluted with 500 ml. of ice water. A cold solution of 5 g. of sodium hydroxide in 100 ml. of water is added and the mixture extracted with two 150 ml. portions of methylene chloride. The organic phase is then washed with 50 ml. of ice water, dried overnight with anhydrous sodium sulfate, filtered and freed of solvent by distillation under reduced pressure.

b. The residue oil from (a.) is taken up in 200 ml. of anhydrous ethyl alcohol previously saturated at 0° C. with dry ammonia gas, mixed with 5 ml. of sponge nickel catalyst suspension and hydrogenated at 25° C. under 100 psi hydrogen pressure in a stirred autoclave. The reaction completion is readily determined by disappearance of the C≡N IR absorption band and measurement of hydrogen uptake. The catalyst is removed by suction filtration, the solvent with mild heating under reduced pressure and the product obtained pure with fractional distillation at reduced pressure.

PREPARATION L

N,N-Di-(2,3-dihydroxypropyl)trimethylenediamine

Bis-(2,3-dihydroxypropyl)amine (16.5 g., 0.1 mole) and acrylonitrile (6.4 g., 0.12 mole) was mixed in an ice bath and then warmed to room temperature. After standing for 2 hours, the mixture was then heated at 45° C.–55° C. for 3 hours. The excess acrylonitrile was removed by gentle warming under reduced pressure. The residue was taken up in ethyl alcohol, mixed with sponge nickel catalyst and hydrogenated under 200 psi hydrogen using good agitation. After filtration of catalyst the solvent and excess acrylonitrile was removed by stripping under reduced pressure to leave the product as an oil.

PREPARATION M

N,N,N'-Tri-(2,3-dihydroxypropyl)trimethylenediamine

N,N-di-(2,3-dihydroxypropyl)trimethylenediamine (11.1 g., 0.05 mole) was dissolved in 125 ml. of methanol and heated under reflux with agitation. Glycidol (3.7 g., 0.05 mole) was added dropwise over a period of 1.5 hour and the solution mixed an additional hour at 60° C.–80° C. The methyl alcohol and other volatiles were removed by stripping under reduced pressure to leave the product suitable for use in the next steps.

PREPARATION N 5,9,9-Tri-(2,3-dihydroxypropyl)-1,5,9-triazanonane

An aliquot of the residual oil from Preparation M (5.9 g., 0.02 mole) was mixed with acrylonitrile (2.75 g., 0.05 mole) at room temperature and then warmed at 50° C.–60° C. for 10–15 hours. The excess acrylonitrile was removed by stripping under reduced pressure and the residual oil taken up in 50 ml. of ethanol, mixed with 2 g. of sponge nickel catalyst and shaken under a hydrogen atmosphere of 200 psi for 6 hours. The mixture was filtered free of catalyst and the solvent removed by distillation. The product could be brought to analytical purity by chromatography on a silica gel column and is an oil.

EXAMPLE 1

Preparation of 1-[1,5-Di-(4-isopropylcyclohexyl)-3-pentyl]1,5,9-triazanone 1.5-Di-(4-isopropylcyclohexyl)-3-pentanone (6.70 g., 0.02 mole) and 3,3'-iminobispropylamine (13.1 g., 0.10 mole) in 150 ml. toluene is heated at reflux overnight with a Dean-Stark water separator. The cooled solution is concentrated under reduced pressure. The residue is dissolved in ethanol and hydrogenated with $PtO_2$ at room temperature and 40 psi hydrogen pressure. The platinum catalyst is filtered off and the ethanol removed under vacuum. The residual oil is dissolved in ether and the ether solution washed several times with water to remove the excess 3,3'-iminobispropylamine. The ether extracts are dried over anhydrous sodium sulfate and concentrated under vacuum to leave the polyamine as a colorless oil.

The oil is dissolved in ether and hydrogen chloride gas is bubbled into the solution until no further precipitation occurs. The ether is evaporated under reduced pressure to leave the product as a solid which is digested with hot isopropyl alcohol. The solids are collected by filtration and dried under vacuum at 70° C. to give a colorless product, 1-[1,5-di-(4-isopropylcyclohexyl)-3-pentyl]-1,5,9-triazanone trihydrochloride.

In an analogous manner, from the ketones and the amines set forth below, there are prepared the following compounds of this invention:

TABLE I

| Ketone | Amine | Product | Melting Point |
|---|---|---|---|
| 1,9-Dicyclohexyl-5-nonanone | 3,3'-Iminobispropylamine | 1-[1,9-Dicyclohexyl-5-nonyl]-1,5,9-triazanonane trihydrochloride | Dec. 183°–187° C. to pulp; 255°–267° C. to liquid |
| 1,5-Dicyclohexyl-3-pentanone | Ethylenediamine | N-[1,5-Dicyclohexyl-3-pentyl]-ethylenediamine dihydrochloride | 261°–263° C. |
| 1,5-Dicyclohexyl-3-pentanone | N-(3-Aminopropyl)-N-methyl-1,3-propane diamine | 1-[1,5-Dicyclohexyl-3-pentyl]-5-methyl-1,5,9-triazanonane trihydrochloride | 247°–249° C. |
| 1,3-Dicyclohexylacetone | 2-Hydroxy-1,3-diaminopropane | N[1,3-Dicyclohexyl-2-propyl]-2-hydroxy-1,3-diaminopropane dihydrochloride | Melts 200° C. with softening from 147° C. |
| 1,5-dicyclohexyl-3-pentanone | 1,3-Diaminopropane | N-[1,5-Dicyclohexyl-3-pentyl]-trimethylenediamine dihydrochloride | 245°–250° C. |
| 1,5-Dicyclohexyl-3-pentanone | 2-Hydroxy-1,3-diaminopropane | 1-Amino-3-[(1,5-dicyclohexyl)-3-pentylamino]-2-propanol dihydrochloride | 250°–252° C. |

TABLE I-continued

| Ketone | Amine | Product | Melting Point |
|---|---|---|---|
| 1,7-Dicyclohexyl-4-heptanone | Iminobispropylamine | 1-(1,7-Dicyclohexyl-4-heptyl)-1,5,9-triazanonane trihydrochloride | 260°–261° C. |
| 1,5-Dicyclohexyl-3-pentanone | Iminobispropylamine | 1-(1,5-Dicyclohexyl-3-pentyl)-1,5,9-triazanonane trihydrochloride | Dec. 224°–228° C. to pulp; 242°–246° C. to liquid |
| 1,5-Dicyclohexyl-3-pentanone | Triethylenetetramine | 1-(1,5-Dicyclohexyl-3-pentyl)-1,4,7,10-tetraazadecane | |

EXAMPLE 2

Preparation of 1-[1,5-Di-(4-isopropylcyclohexen-1-yl)-3-pentyl]-1,5,9-triazanonane 1,5-(4-isopropylcyclohexen-yl)-3-pentanone, (6.60 g., 0.02 mole) and 3,3'-iminobispropylamine (13.1 g., 0.10 mole) in 150 ml. of toluene is heated at reflux overnight with a Dean-Stark water separator. The toluene is then removed under vacuum. The residual oil dissolved in 25 ml. isopropanol is added dropwise to sodium borohydride (1.90 g., 0.05 mole, excess) suspended in 50 ml. isopropanol. After complete addition, the reaction mixture is heated at reflux for one hour. The isopropanol is evaporated under reduced pressure, the residue treated with water and the aqueous mixture extracted well with ether. The combined ether extracts are back-washed with water, a saturated sodium chloride solution, dried over anhydrous sodium sulfate and concentrated under vacuum to leave the polyamine product as a clear oil 7.4 g. (90%).

The oil is dissolved in ether and the solution cooled in an ice-water bath. Hydrogen chloride gas is bubbled into the solution until no further precipitate is formed. The solid is collected by filtration, washed with a small amount of ether, and dried under vacuum to leave the polyamine trihydrochloride as a colorless product (96%), m.p. 256°–257° C.

In an analogous manner using the ketones and the amines set forth below the following compounds of this invention are prepared.

mole) in 250 ml. ethanol is heated at reflux overnight. The cooled reaction mixture is hydrogenated with $PtO_2$ at room temperature and 40 psi hydrogen pressure. The platinum catalyst is filtered off and the ethanol removed under reduced pressure. The residual oil is dissolved in ether and the ether solution washed several times with water to remove the excess diaminoethane. The ether extracts are dried over anhydrous sodium sulfate and concentrated under vacuum to leave a colorless oil, 11.2 g. (100%).

The oil is dissolved in 20 ml. tert-butanol and chilled to 0° C.-5° C. in an ice-water bath. Acrylonitrile (1.75 g., 2.2 ml., 0.033 mole) is added dropwise over a 5-minute period. The reaction mixture is allowed to warm up to room temperature and is then heated at 60° C. overnight. The t-butanol was removed under reduced pressure. The residual oil was dissolved in 150 ml. glacial acetic acid and hydrogenated with $PtO_2$ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure to leave the product.

In addition, the compounds of this invention set forth below are prepared by the reactions set forth in the previous examples.

1-[1,9-Dicyclohexyl-5-nonyl]-1,5,8,12-tetrazadodecane from N,N'-bis-(3-aminopropyl)-1,2-ethanediamine

TABLE II

| Ketone | Amine | Product | Melting Point |
|---|---|---|---|
| 1,7-Di-(cyclohex-3-enyl)-4-heptanone | Iminobispropylamine | 1-[1,7-Di-(cyclohex-3-enyl)-4-heptyl]-1,5,9-triazanonane trihydrochloride | 222°–223° C. |
| 2,8-Di-(4-methylcyclohex-3-enyl)-5-nonanone | Iminobispropylamine | 1-[2,8-Di-(4-methylcyclohex-3-enyl)-5-nonyl]-1,5,9-triazanonane trihydrochloride | 269°–271° C. |
| 1,5-Di-[4-(isopropyl)cyclohex-1-enyl]-3-pentanone | Triethylenetetramine | 1-[1,5-Di-(4-isopropylcyclohex-1-enyl)-3-pentyl]-1,4,7,10-tetrazadecane tetrahydrochloride | 229°–230° C. |
| 2,8-Di-(4-methylcyclohex-3-enyl)-5-nonanone | Tris-(3-aminopropyl)-amine | 1-[2,8-Di-(4-methylcyclohex-3-enyl)-5-nonyl]-5-(3-aminopropyl)-1,5,9-triazanonane | |
| 1,7-Di(cyclohex-3-enyl)-4-heptanone | 1,4-Bis-(3-aminopropyl)-piperazine | 1-(3-Aminopropyl)-4-(3-[1,7-di-(cyclohexen-3-yl)-4-heptylamino]propyl]piperazine | |
| 1,7-Di(cyclohex-3-enyl)-4-heptanone | 1,4-Di-(3-aminopropyl)-piperidine | A mixture of 1-(3-aminopropyl)-4-[3-[1,7-di-(cyclohexen-3-yl-4-heptylamino]propyl]piperidine and 1-[3-[1,7-di(cyclohexen-3-yl-4-heptylamino]propyl]-4-(3-aminopropyl)piperidine | |
| 1,5-Di-(4-isopropylcyclohexenyl)-3-pentanone | N,N'-bis-(2-aminoethyl)-1,3-propanediamine | 1-[1,5-Di-(4-isopropylcyclohexenyl)-3-pentyl]-1,4,8,11-tetrazaundecane | |

EXAMPLE 3

1-[1,7-Di-(4-methylcyclohexyl)-4-heptyl]-1,4,8-triazaoctane

A mixture of 1,7-di-(4-methylcyclohex-3-enyl)-4-heptanone (0.03 mole) and 1,2-diaminoethane (12.0 g., 0.20 and 1,9-dicyclohexyl-5-nonanone;

1-[1,5-Dicyclohexyl-3-pentyl]-10-(2-hydroxyethyl)-1,4,7,10-tetrazadecane from 1-(2-hydroxyethyl)-1,4,7,10-tetrazadecane and 1,5-dicyclohexyl-3-pentanone;

1-[1,5-Dicyclohexyl-3-pentyl]-4-(2-aminoethyl)-1,4,7-triazaheptane from tris-(2-aminoethyl)amine and 1,5-dicyclohexyl-3pentanone;

1-[1,5-Dicyclohexyl-3-pentyl]-5-(2-hydroxypropyl)-9-hydroxymethyl-1,5,9-triazanonane from 1-hydroxymethyl-5-(2-hydroxypropyl)-1,5,9-triazanonane and 1,5-dicyclohexyl-3-pentanone.

EXAMPLE 4

Preparation of 1-[1,5-Di-(4-isopropylcyclohexyl)-3-pentyl]-5-(2,3-dihydroxypropyl)-1,5,9-triazanonane 1,5-Di-(4-isopropylcyclohexyl)-3-pentanone (6.7 g., 0.02 mole) and 3,3'-(2,3-dihydroxypropylimino)bispropylamine (20.5 g., 0.10 mole), (obtained by the catalytic hydrogenation of dicyanoethylated glycerylamine,) in 150 ml. of toluene is heated at reflux overnight with a Dean-Stark water separator. The cooled solution is concentrated under reduced pressure. The residue is dissolved in ethanol and hydrogenated with PtO₂ at room temperature and 40 psi hydrogen pressure. The platinum catalyst is filtered off and the ethanol removed under vacuum. The residual oil is dissolved in ether and the ether solution washed several times with water to remove the excess 3,3'-(2,3-dihydroxypropylimino)bispropylamine. The ether extracts are dried over anhydrous sodium sulfate and concentrated to leave the polyamine product as an oil.

In a like manner and using analogous quantities, but employing N,N-di-(2,3-dihydroxypropyl)trimethylenediamine and 5,9,9-tri-(2,3-dihydroxypropyl)-1,5,9-triazanonane instead of 3,3'-(2,3-dihydroxypropylimino)bispropylamine there are prepared respectively N-[1,5-di-(4-isopropylcyclohexyl)-3-pentyl]-N'-di-(2,3-dihydroxypropyl)trimethylenediamine, and 1-[1,5-di-(4-isopropylcyclohexyl)-3-pentyl]-5-(2,3-dihydroxypropyl)-9-di-(2,3-dihydroxypropyl)-1,5,9-triazanonane.

EXAMPLE 5

Preparation of 1-[1,5-Di-(4isopropylcyclohexyl)-3-pentyl]-5-(2,3-dihydroxypropyl)-9-(1,3-dihydroxyl-2-propyl)-1,5,9-triazanonane 1-[1,5-Di-(4-isopropylcyclohexyl)-3-pentyl]-5-(2,3-dihydroxypropyl)-1,5,9-triazanonane (5.2 g., 0.01 mole) and 1,3-dihydroxyacetone (9 g., 0.1 mole) in 100 ml. of chloroform was heated at reflux with a water separator connected until 1.8 ml. of water was collected (8–12 hours). The chloroform and excess 1,3-dihydroxyacetone were removed by distillation under reduced pressure. The residual oil was taken up in 75 ml. of ethanol, mixed with 1 gm. of platinum oxide and hydrogenated at 40 psi hydrogen pressure with shaking at room temperature. The catalyst was removed by filtration and ethyl alcohol by distillation to leave an oil. The product could be purified by column chromatography using silica gel and development with methyl alcohol containing ammonium hydroxide.

In an analogous manner but starting with 1,7-di-(2,3-dimethylcyclohexyl-4-heptyl)ethylenediamine, instead of 1-[1,5-di-(4-isopropylcyclohexyl)-3-pentyl]-1,5,9-triazanonane thereis obtained N-[1,7-di-(2,3-dimethylcyclohexyl)-4-heptyl]-N'-(1,3dihydroxy-2-propyl)ethylenediamine.

EXAMPLE 6

1-[1,7-Di-(4-methylcyclohexyl)-4-heptyl]-4,8,8-tri-(2,3-dihydroxypropyl)-1,4,8-triazaoctane 1-[1,7-Di-(4-methylcyclohexyl)-4-heptyl]-1,4,8-triazaoctane (4.1 g., 0.01 mole) was dissolved in 50 ml. of methanol and heated under reflux with agitation. Glycidol (15 g., 0.2 mole) was added dropwise over a period of 1.5 - 2 hours. After complete addition, the reaction mixture was stirred an additional 2 hours at 90° C.-100° C. The methyl alcohol was removed by stripping under reduced pressure and excess glycidol by distillation at 1 mm pressure. The residue could be further purified by conversion to the trihydrochloride salt in ethyl alcohol with dry hydrogen chloride and fractional crystallization. The free base may then be liberated from its salt by resin ion exchange or neutralization with aqueous sodium hydroxide.

In an analogous manner using the following dicyclohexyl polyamines, there are obtained the following products.

| Dicyclohexyl Polyamine | Product |
|---|---|
| 1-[1,5-Di-(4-isopropylcyclohexyl-3-pentyl]-3,7-dihydroxy-1,5,9-triazanonane | 1-[1,5-Di-(4-isopropylcyclohexyl)-3-pentyl]-3,7-dihydroxy-5-(2,3-dihydroxypropyl)-9,9-di-(2,3-dihydroxypropyl)-1,5,9-triazanonane |
| 1-[1,5-Di-(4-isopropylcyclohexyl)-3-pentyl]-1,4,7-triazaheptane | 1-[1,5-Di-(4-isopropylcyclohexyl)-3-pentyl]-4-(2,3-dihydroxypropyl)-7,7-di-(2,3-dihydroxypropyl)-1,4,7-triazaheptane |
| 1-[1,5-Di-(4-isopropylcyclohexyl)-3-pentyl]ethylenediamine | N-[1,5-Di-(4-isopropylcyclohexyl)-3-pentyl]-N',N-di-(2,3-dihydroxypropyl))ethylenediamine |

Also each of the respective ketones IV set forth in Preparations C and D when reacted with each of the individual amines set forth hereinbefore firstly, according to the method set forth in Example 1, and then second according to Example 2 produce the entire range of compounds described according to this invention as embodied in Formula I.

What is claimed is:

1. An antibacterial composition comprising an admixture of 1 to 500 parts by weight of tris(hydroxylamine)methylamine for each part by weight of a polyamine having the formula:

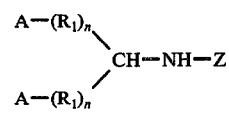

where A is alike or different cyclohexyl or cyclohexenyl of the formula:

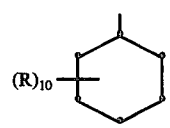 or 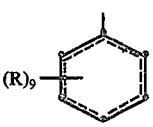

where
each R is either hydrogen or $C_1$ to $C_6$ alkyl, and the dished line indicates a single obefinic bond;
each $n$ is alike or different and is the integer 0 or 1;

each $R_1$ is alike or different and is $C_1$ to $C_4$ alkylene; Z is

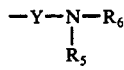

where
$R_5$ is hydrogen, aminoethyl, aminopropyl, $C_1$ to $C_4$ hydroxyalkyl, or $C_2$ to $C_4$ dihydroxyalkyl; and
$R_6$ is hydrogen, $C_1$ to $C_4$ hydroxyalkyl or $C_2$ to $C_4$ dihydroxyalkyl;

a. when Y is

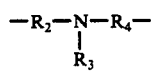

$R_2$ is 2-hydroxy-1,3-trimethylene, or $R_1$ as previously defined;
$R_3$ is hydrogen, $C_1$ to $C_4$ alkyl, $C_2$ to $C_4$ aminoalkyl, $C_1$ to $C_4$ hydroxyalkyl, or $C_2$ to $C_4$ dihydroxyalkyl;
$R_4$ is 2-hydroxy-1,3-trimethylene, or $R_1$ as previously defined;
or when $R_3$ and $R_6$ taken together are ethylene, $R_4$ is also ethylene, and $R_5$ is aminoethyl, aminopropyl, or aminohydroxypropyl; and b. when Y is

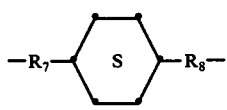

$R_7$ is $R_2$, methylene, or a chemical bond between the cyclohexylene moiety and a first nitrogen; $R_8$ is $R_4$, methylene, or a chemical bond between the cyclohexylene moiety and a second nitrogen; and c. when Y is $-R_2-$, then $R_2$, $R_5$ and $R_6$ are as previously defined, or acid addition salts thereof.

2. The composition according to claim 1 where $n$ is 1.
3. The composition according to claim 2 where $R_1$ is methylene.
4. The composition according to claim 2 where $R_1$ is ethylene.
5. The composition according to claim 2 where $R_1$ is trimethylene.
6. The composition according to claim 1 where Z is

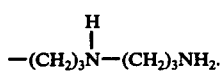

7. The composition according to claim 1 where Z is $-(CH_2)_2NH_2$.
8. The composition according to claim 1 where Z is

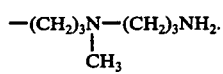

9. The composition according to claim 1 where Z is $-CH_2CHOHCH_2NH_2$.
10. The composition according to claim 1 where Z is $-(CH_2)_3NH_2$.
11. An antibacterial composition comprising 1 to 500 parts by weight of tris-(hydroxymethyl)aminomethane for each part by weight of a compound of the formula:

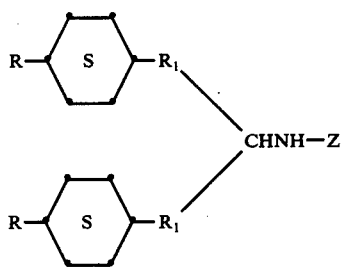

where
R is hydrogen, methyl or isopropyl;
$R_1$ is methylene, ethylene, trimethylene or tetramethylene;
and where Z is:
—$(CH_2)_3NH(CH_2)_3NH_2$;
—$(CH_2)_2NH(CH_2)_2NH(CH_2)_2NH_2$;
—$(CH_2)_3NCH_3(CH_2)_3NH_2$;
—$CH_2CHOHCH_2NH_2$;
—$(CH_2)_2NH_2$; or
—$(CH_2)_3NH_2$; or acid addition salts thereof.

12. The composition according to claim 11 where the polyamine is 1-(1,5-dicyclohexyl-3-pentyl)-1,5,9-triazanonane or salts thereof.
13. The composition according to claim 11 where the polyamine is 1-(1,7-dicyclohexyl-4-heptyl)-1,5,9-triazanonane or salts thereof.
14. The composition according to claim 11 where the polyamine is 1-(1,5-dicyclohexyl-3-pentyl)-1,4,7,10-tetrazadecane or salts thereof.
15. The composition according to claim 11 where the polyamine is 1-(1,5)-di-(4-isopropylcyclohexyl-3-pentyl)-1,5,9-triazanonane or salts thereof.
16. The composition according to claim 11 where the polyamine is 1-(1,5-dicyclohexyl-3-pentyl)-3-hydroxy-1,5-diazapentane or salts thereof.
17. The composition according to claim 16 where the polyamine is the dihydrochloride acid addition salt.
18. The composition according to claim 16 where the polyamine is the dipropionate salt.
19. The composition according to claim 11 where the polyamine is N-(1,5-dicyclohexyl-3-pentyl)ethylenediamine.
20. The composition according to claim 19 where the polyamine is the dihydrochloride acid addition salt.
21. An antibacterial composition comprising 1 to 500 parts by weight of tris-(hydroxymethyl)aminomethane for each part by weight of a compound of the formula:

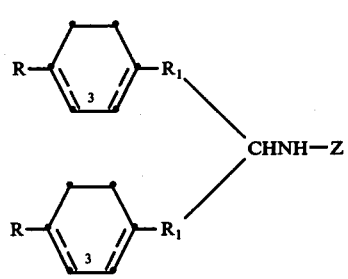

where

R is hydrogen, methyl or isopropyl;
R$_1$ is C$_1$ to C$_4$ alkylene;
the dashed line indicates cyclohexenyl or cyclohex-3enyl;
and Z is
—(CH$_2$)$_3$NH(CH$_2$)$_3$NH$_2$;
—(CH$_2$)$_2$NH(CH$_2$)$_2$NH(CH$_2$)$_2$NH$_2$;
—(CH$_2$)$_3$NCH$_3$(CH$_2$)$_3$NH$_2$;
—CH$_2$CHOHCH$_2$NH$_2$;
—(CH$_2$)$_3$NH$_2$; or and —(CH$_2$)$_2$NH$_2$; or acid addition salts thereof.

22. The composition according to claim 21 where the polyamine is 1-[1,5-di-(4-isopropylcyclohexen-1-yl)-3-pentyl]-1,5,9-triazanonane.

23. The composition according to claim 21 where the polyamine is 1-[1,5-di-(4-isopropylcyclohexen-1-yl)-3-pentyl]-1,4,7,10-tetrazadecane.

24. The composition according to claim 21 where the polyamine is 1-[2,8-di-(4-methylcyclohex-3-enyl)-5-nonyl]-1,5,9-triazanonane.

* * * * *